United States Patent [19]

Benin et al.

[11] Patent Number: 4,521,263
[45] Date of Patent: Jun. 4, 1985

[54] AUTOMATIC SPLICING DEVICE AND PROCESS

[75] Inventors: Joshua Benin; Helen R. Delp, both of Newark, Del.; Leland L. Krauss, Aston, Pa.

[73] Assignee: E. I. Du Pont de Nemours and Company, Wilmington, Del.

[21] Appl. No.: 637,581

[22] Filed: Aug. 3, 1984

Related U.S. Application Data

[63] Continuation-in-part of Ser. No. 408,418, Aug. 16, 1982, abandoned.

[51] Int. Cl.³ .................. A61M 5/00; B29C 27/00
[52] U.S. Cl. ........................... 156/159; 156/304.2; 156/503; 604/905
[58] Field of Search ............... 156/157, 158, 159, 502, 156/503, 304.2, 304.6, 309.1, 251, 353, 433, 304.5; 604/905, 403

[56] References Cited

U.S. PATENT DOCUMENTS

| | | |
|---|---|---|
| 336,528 | 2/1886 | Puetz . |
| 2,384,014 | 9/1945 | Cutter . |
| 2,647,555 | 8/1953 | Hinman . |
| 3,391,045 | 7/1968 | Mojonnier et al. . |
| 3,729,360 | 4/1973 | McElroy . |
| 3,769,124 | 10/1973 | Johnson . |
| 3,897,296 | 7/1975 | Waldrum . |
| 3,968,195 | 7/1976 | Bishop . |
| 4,263,084 | 4/1981 | Takala . |
| 4,369,774 | 1/1983 | Spencer . |

FOREIGN PATENT DOCUMENTS 2250130 4/1974 Fed. Rep. of Germany .

Primary Examiner—Michael Ball

[57] ABSTRACT

An apparatus, system, and process for making a sterile connection between two thermoplastic resin tubes is disclosed. The tubes are cut by a hot cutting means so as to form a molten interface between the tubes and the cutting means. The tubes are aligned with each other and slid off an edge of the cutting means while being urged together. As the thermoplastic resin cools a sterile splice is formed. The apparatus is controlled to provide precise timing of the above events and includes safeguards to ensure sterility is maintained.

12 Claims, 20 Drawing Figures

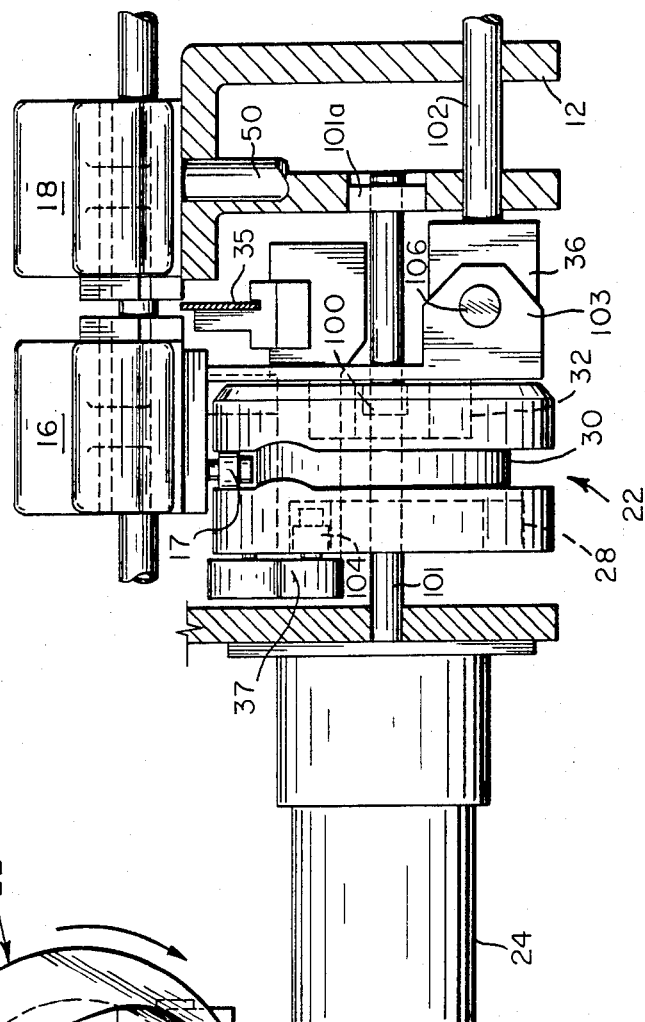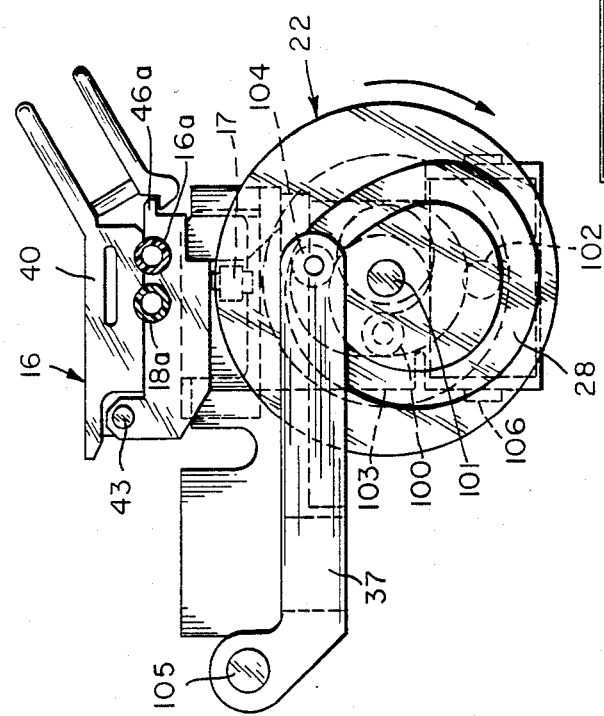

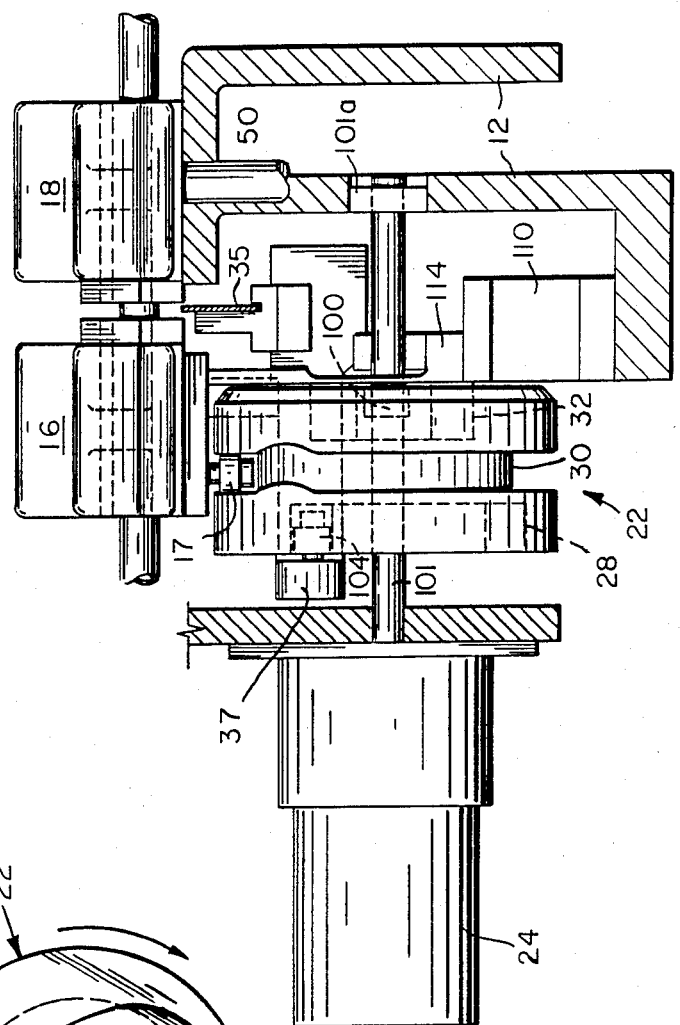
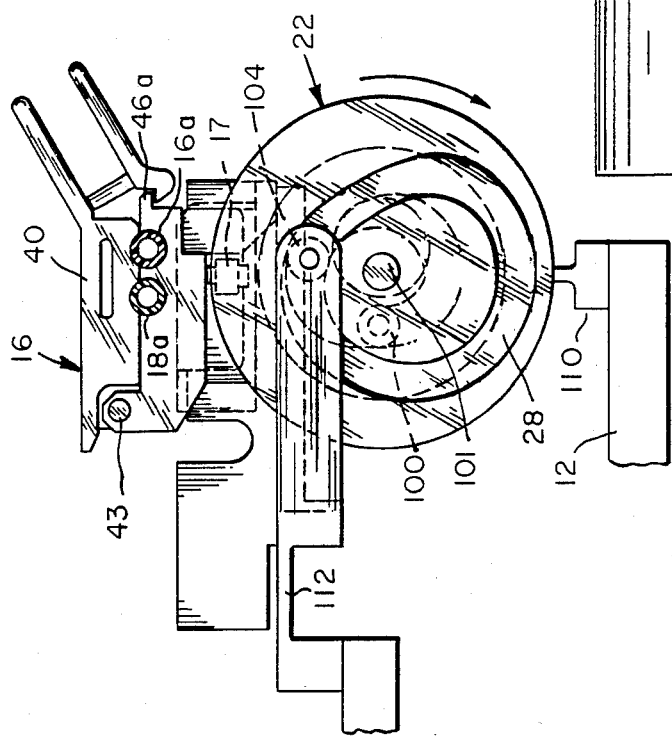

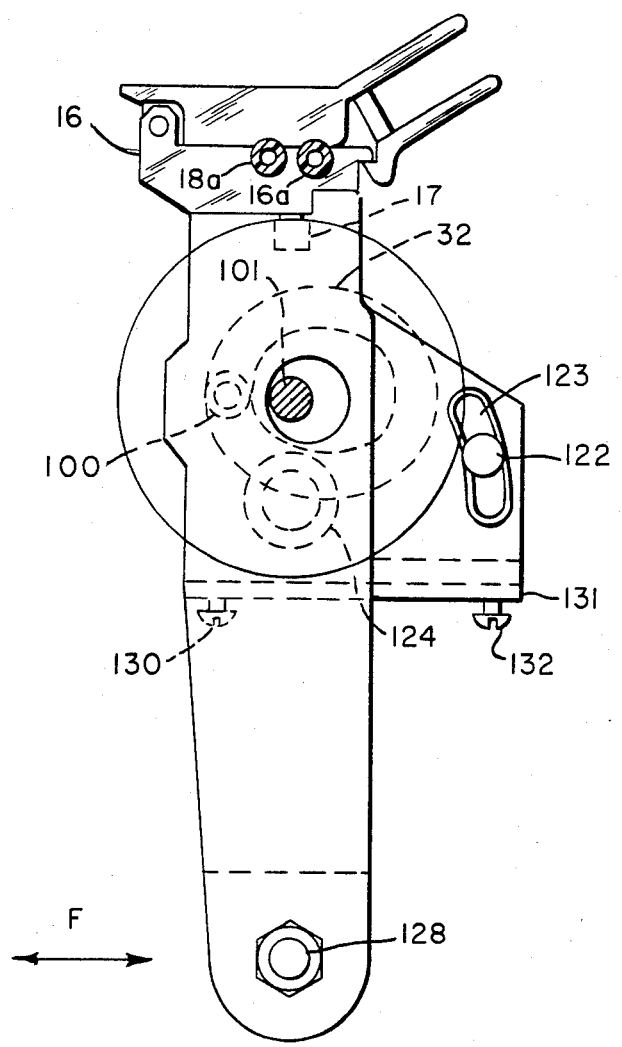

AUTOMATIC SPLICING DEVICE AND PROCESS

BACKGROUND OF THE INVENTION

This is a continuation-in-part of application Ser. No. 408,418, filed Aug. 16, 1982 and now abandoned.

This invention relates to an apparatus, system and process for forming a sterile connection between two plastic tubes.

At the present time there are a number of medical and scientific procedures which require the sterile transfer of fluids from one container to another. Two areas in which sterile splicing of tubes would be useful are in replacing dialysate liquid bags in continuous ambulatory peritoneal dialysis (CAPD) procedures, and in processing blood in bags to separate components, add treating agents, etc.

A splicing device which would automatically produce sterile splices between two internally sterile tubes in a simple, rapid, reliable manner would permit one to effect whatever processing is desired in such areas without compromising sterility.

SUMMARY

The present invention relates to an apparatus, system and process for cutting and joining two internally sterile tubes using a heated cutting means while maintaining system sterility. The tubes to be joined are cut by the cutting means with molten polymer sealing each tube end against the cutting means. Seals of molten polymer hot enough to kill bacteria quickly are effectively maintained with no chance for viable airborne or surface bacteria to find their way inside either of the tubes or the joint. The tube ends are moved into alignment, the heated cutting means slid away, and the ends pushed together. When the joint cools, the sterile connection is complete.

The system includes, in addition to the heated cutting means, a pair of mounting blocks adapted to receive and hold the tubes and a family of mechanisms to generate three orthogonal motions required in splicing. These are moving the hot blade and the tubes relative to each other to pass the blade through the tubes, shifting the mounting blocks or clamps holding the tubes relative to each other to align the tube ends to be joined, and finally as the hot blade is moved from contact with the tubes, pushing or urging the mounting blocks together. The system also includes a controller to provide precise timing of the events outlined above for effecting a sterile connection and to provide safeguards to insure sterility is maintained.

BRIEF DESCRIPTION OF THE DRAWINGS

FIG. 3 is a view of FIG. 2 taken along line 3—3.

FIG. 4 is a view of FIG. 2 taken along line 4—4.

FIG. 10 is a view of FIG. 9 taken along line A—A.

FIG. 11 is a view of FIG. 9 taken along line B—B.

FIGS. 12 and 13 represent a third embodiment with views similar to FIGS. 3 and 4 showing the replacement of one pivot with a flexure.

DETAILED DESCRIPTION OF THE INVENTION

Figure 1:
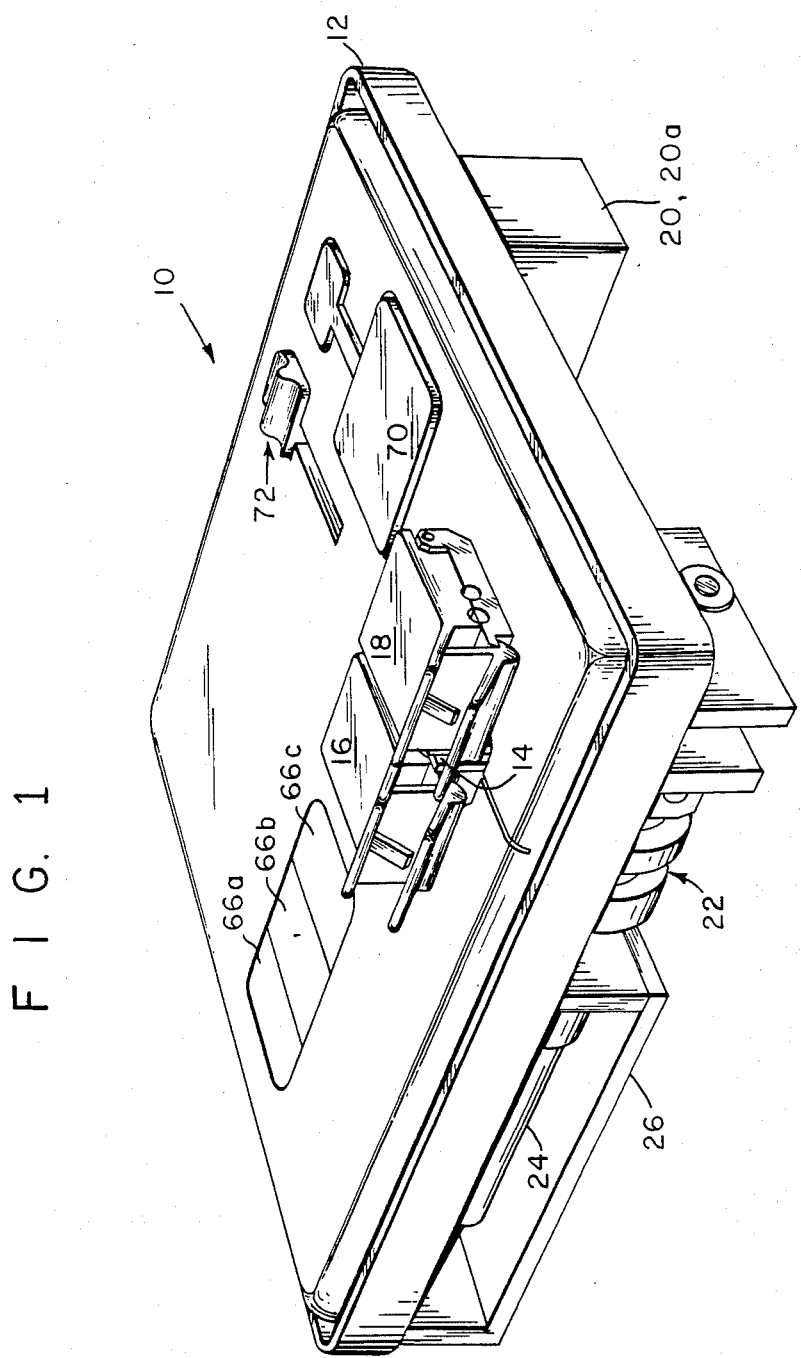
FIG. 1 is an isometric view of the automatic splicing device of this invention.

Referring to FIG. 1, the splicing device chosen for purposes of illustration is denoted generally as 10 and includes as major components a frame 12, a cutter 14 pivotally connected to the frame, a pair of mounting blocks 16, 18 spaced from each other in the same plane, an evacuation pump 20a driven by a motor 20, a cam cylinder 22 driven by a motor 24 and the electronic control unit 26.

Figure 2:
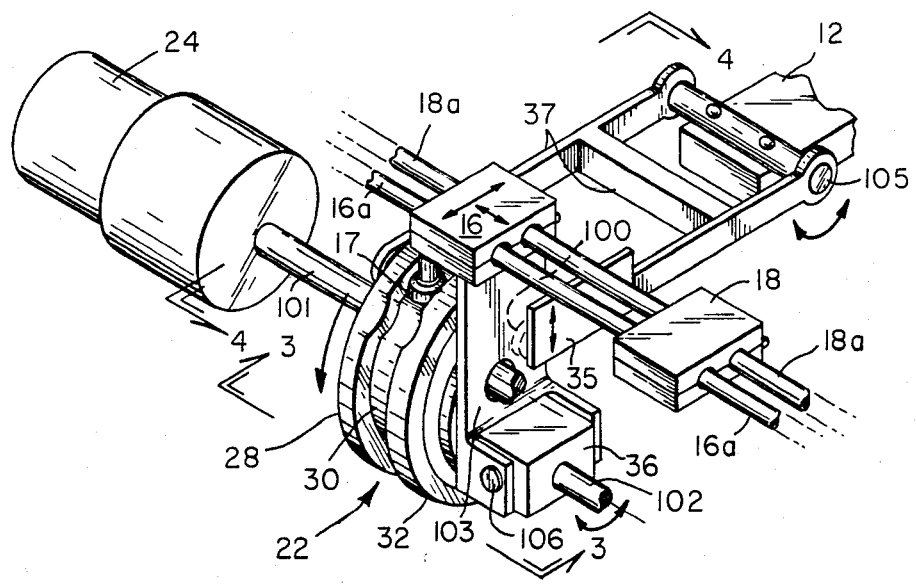
FIG. 2 is an isometric view partially broken away of the driven cam used to move the clamps and the blade of the splicing device of FIG. 1.

The mechanism for generating the three orthogonal motions required for splicing is seen in FIG. 2 which shows a typical arrangement of that mechanism. More particularly, it involves three cams to accomplish the three motions. In the preferred embodiment shown, the cams are grooves 28, 30, 32 on different faces of cam cylinder 22. This arrangement ensures that the three cams never get out of phase. A knife holder 37 for blade 35 is pivotally attached to frame 12 with pivot 105 at one end and is engaged in cam groove 28 at its other end by means of attached follower 104 (FIGS. 3, 4). The blade 35 is positioned between mounting blocks 16, 18 and below the tubes 16a and 18a held side-by-side in the blocks for splicing. A pivoting block 36 is journaled in frame 12 by means of pivot 102 at one end and has supporting structure 103 pivotally attached with pivot 106 at its other end. Support structure 103 has mounting block 16 rigidly attached at the end opposite pivot 106 and is engaged with cam groove 32 intermediate its ends by follower 100. Follower 100 is located adjacent extended motor shaft 101 which supports cam cylinder 22 and passes through a clearance hole in structure 103 from which shaft 101 extends to support bearing 101a in frame 12. Support structure 103 is also engaged in peripheral cam groove 30 via follower 17. When follower 17 moves laterally due to cam groove 30, supporting structure 103 pivots at 106 and causes follower 100 to move perpendicular to but not out of groove 32. Mounting block 18 is fixed to frame 12. Motor 24 rotates cam cylinder 22 via shaft 101.

The blade 35 for the cutting knife is an etched stainless steel foil resistor laminated between sheets of copper connected to a battery. In use, it is subjected to a short heating cycle (about 6 seconds) and to one-shot use (a new blade is used for each splice).

Figure 5A:
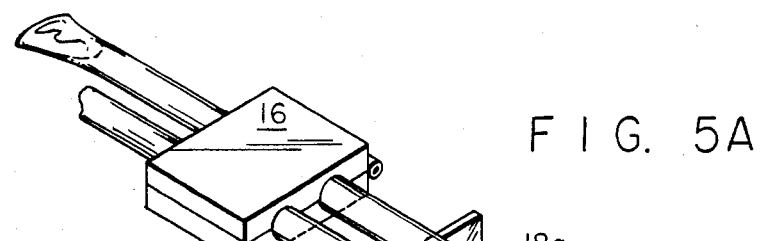
FIGS. 5A-5D are schematic views of two tubes being positioned, severed, realigned and joined, respectively.
Figure 5B:
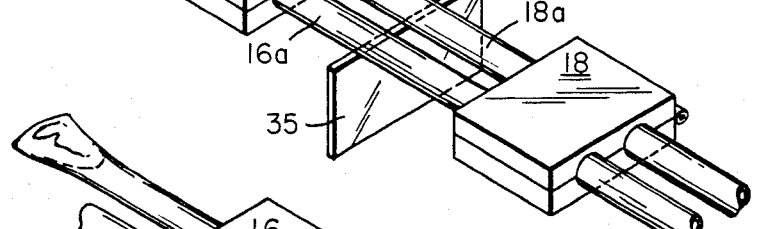
Figure 5C:
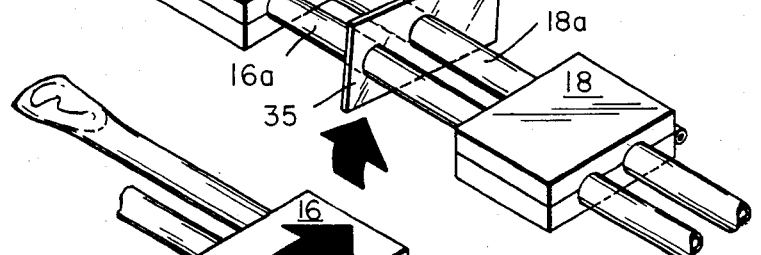
Figure 5D:
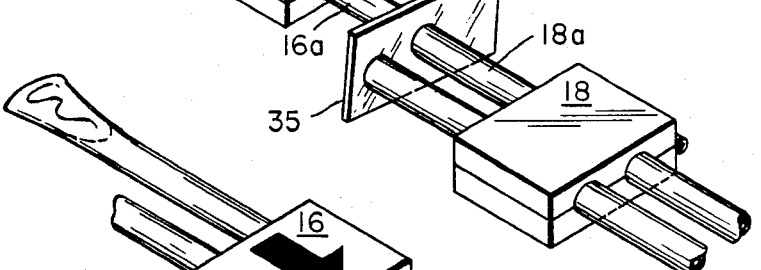

The splicing operation with the apparatus disclosed utilizes three orthogonal motions involving mounting block 16 and the knife blade 35. These are lifting the knife blade 35 through the tubes 16a and 18a, shifting the tubes to align the ones to be joined together and finally urging the tubes together while withdrawing the blade. FIGS. 5A-5D schematically shows this operation and in 5A the mounting blocks 16, 18 and knife blade 35 are shown in the ready position after the blade is heated to operating temperature. The cam cylinder 22 commences rotation (FIG. 4) in the direction of the arrow and with this rotation cam groove 28 lifts knife blade 35 in a first orthogonal motion upwardly through the tubes 16a, 18a (FIG. 5B). With the blade 35 dwelling between the tubes, continued rotation of the cam cylinder causes cam groove 32 to rotate mounting block 16 in a second orthogonal motion aligning the tubes 16a, 18a (FIG. 5C). Continued rotation of the cam cylinder causes peripheral cam groove 30 to urge mounting block 16 toward fixed mounting block 18 as knife blade 35 is lowered. Thus in a third orthogonal motion tubes 16a, 18a are pushed together forming a sterile splice between them (5D).

Figure 6:
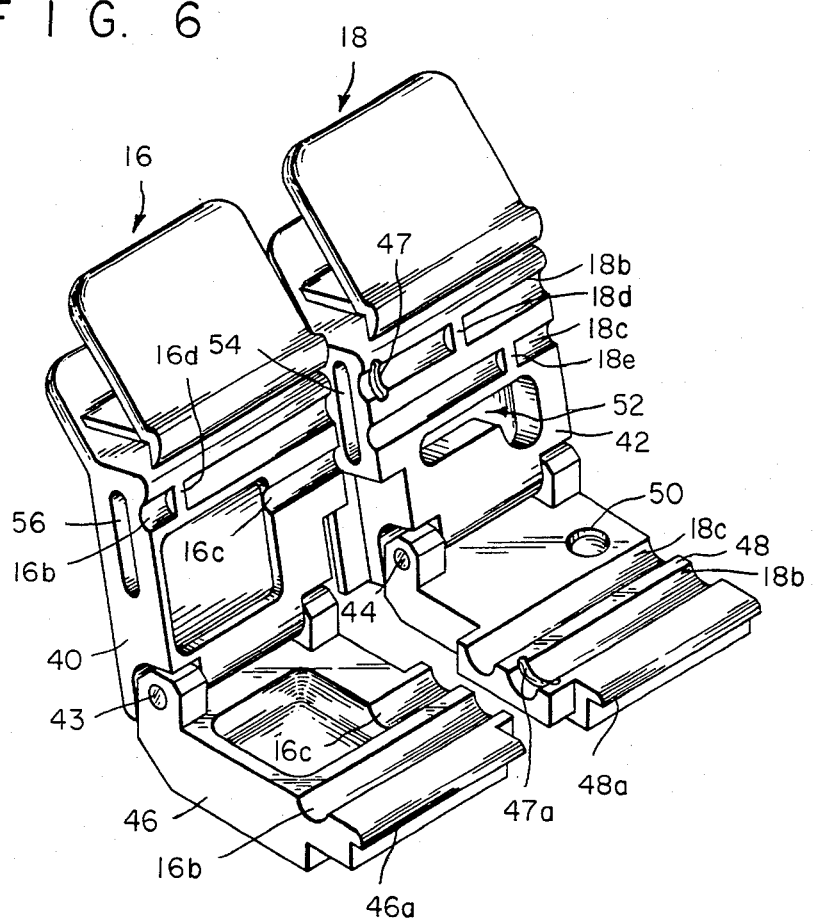
FIG. 6 is an isometric view of the mounting blocks of the splicing device of this invention.

As best shown in FIG. 6, the tube mounting blocks 16, 18 include covers 40, 42 pivotally attached at hinge points 43, 44 to tube holder bases 46, 48. The fixed mounting block 18 has a relief groove 47 cut in its cover 42 with a matching groove 47a in its holder 48 to accommodate an old splice. Channels 16b, 16c are provided in mounting block 16 to hold the tubes to be spliced and mounting block 18 is similarly equipped with channels 18b, 18c. Mounting block 16 is also shown with a closed end to channel 16c to position the tube and permit finger access for removal of the severed off end of tube 18a. The channel 16b in cover 40 is provided with a web 16d and the channels 18b and 18c in cover 42 are provided with webs 18d and 18e for the purpose of clamping the tubes positively in place when the covers are latched in place over the lips 46a and 48a of the respective bases 46, 48. Also incorporated in the mounting block 18 is a passage 50 in the base 48 that is connected to evacuation pump 20a. Passage 50 is in communication with recess 52 in cover 42 and intersecting channel 54 when mounting block 18 is closed to pull air above the tubes as they are being melted by the hot knife 35. The fumes from the splicing operation are drawn off and filtered in a filter (not shown) attached to the inlet of pump 20a. The mounting block 16 also has a channel 56 in its cover 40 to provide a direct path for air to be drawn above the tubes into the cover 42.

Figure 1A:
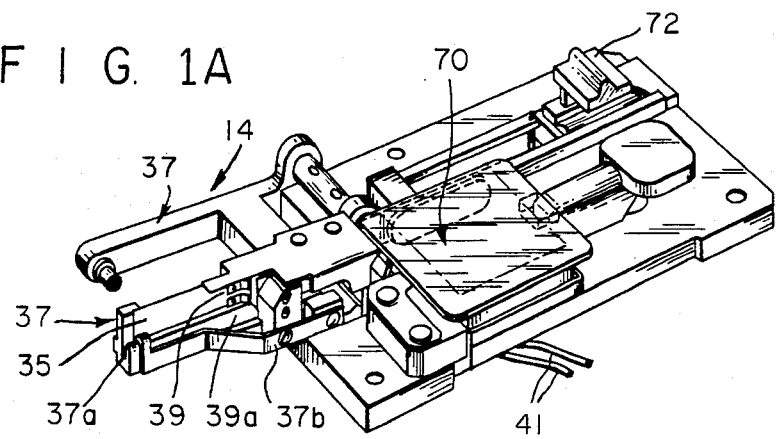
FIG. 1A is an isometric view of the blade holder and load and eject device used in the splicing device of this invention.

The knife blade load and eject system is best seen in FIG. 1A and includes a blade magazine 70, a blade load-eject pusher lever 72, blade holder 37, blade clamp 37b and a track 37a in the blade holder. A pair of spring loaded electrical contacts 39, 39a joined by leads 41 to controller 26 are making contact with the blade 35.

Figure 7:
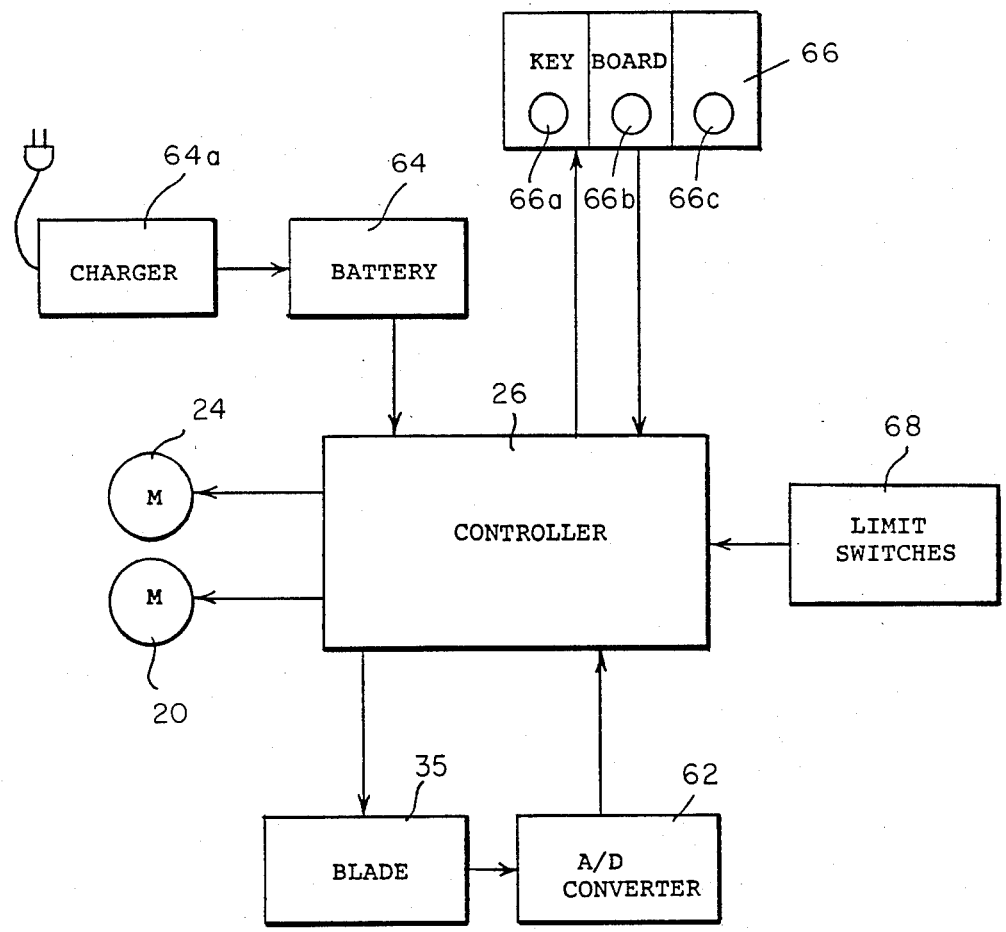
FIG. 7 is a block diagram of the control system for the splicing device of this invention.
Figure 8A:
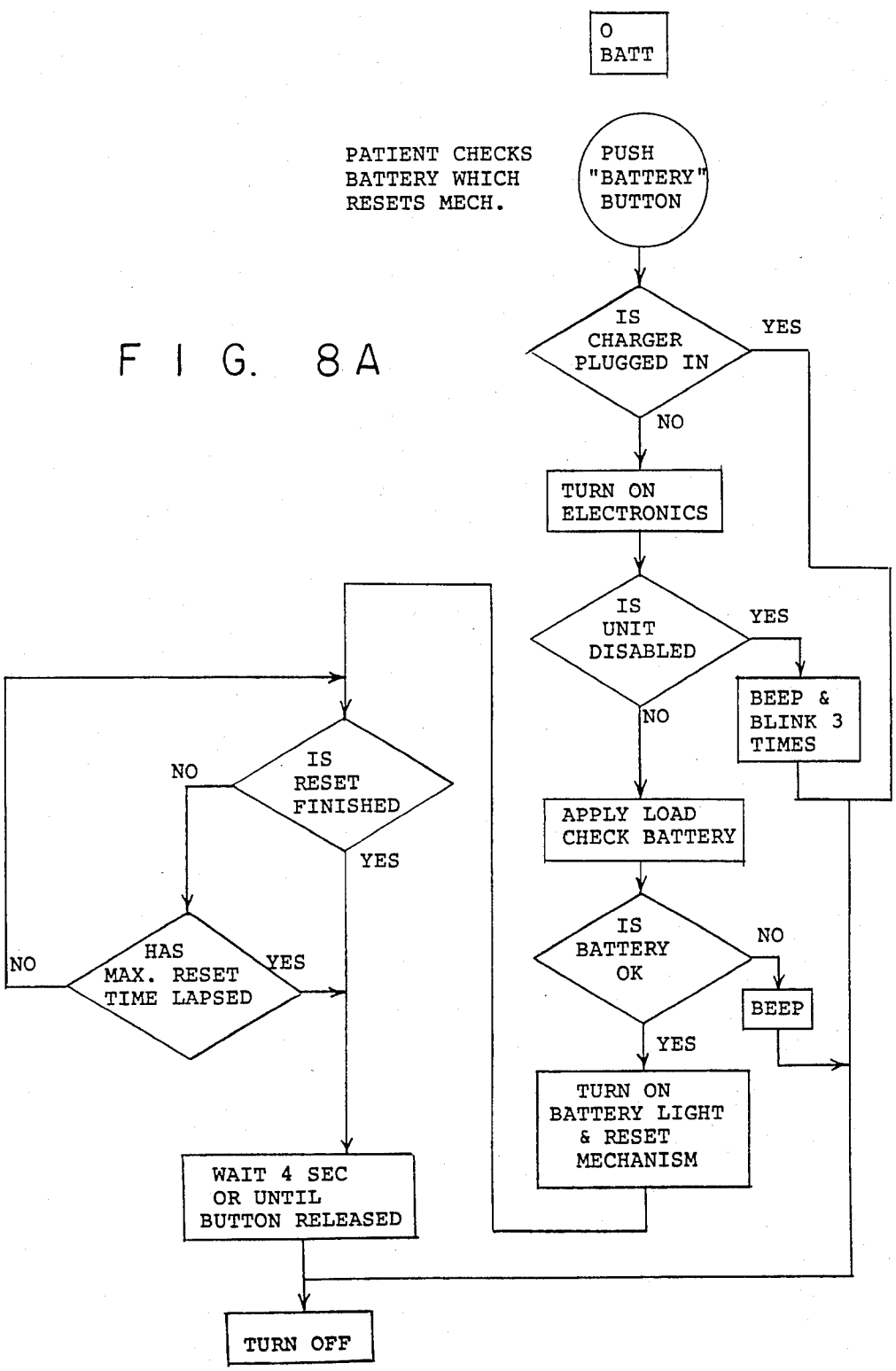
FIGS. 8A-8D are logic diagrams for the splicing device of this invention.
Figure 8B:
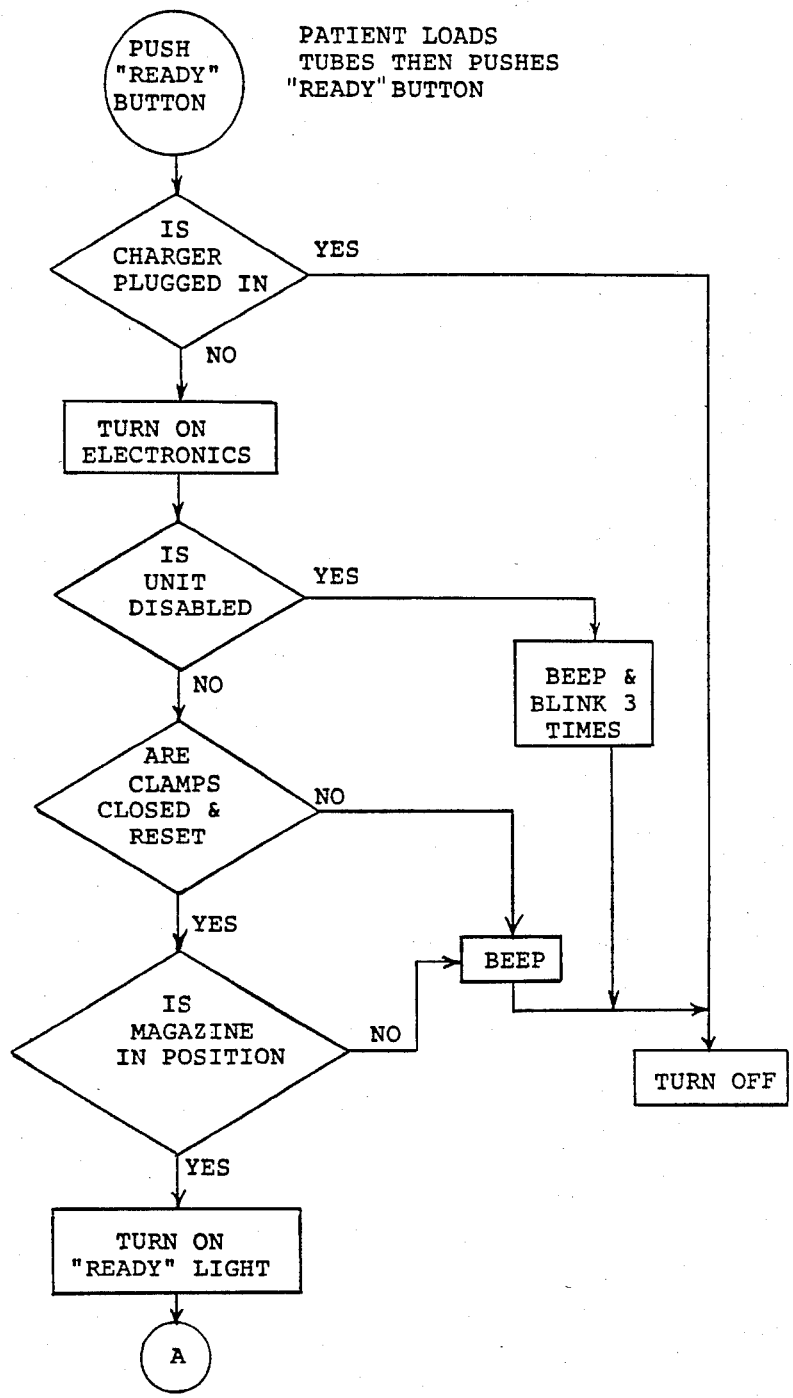
Figure 8C:
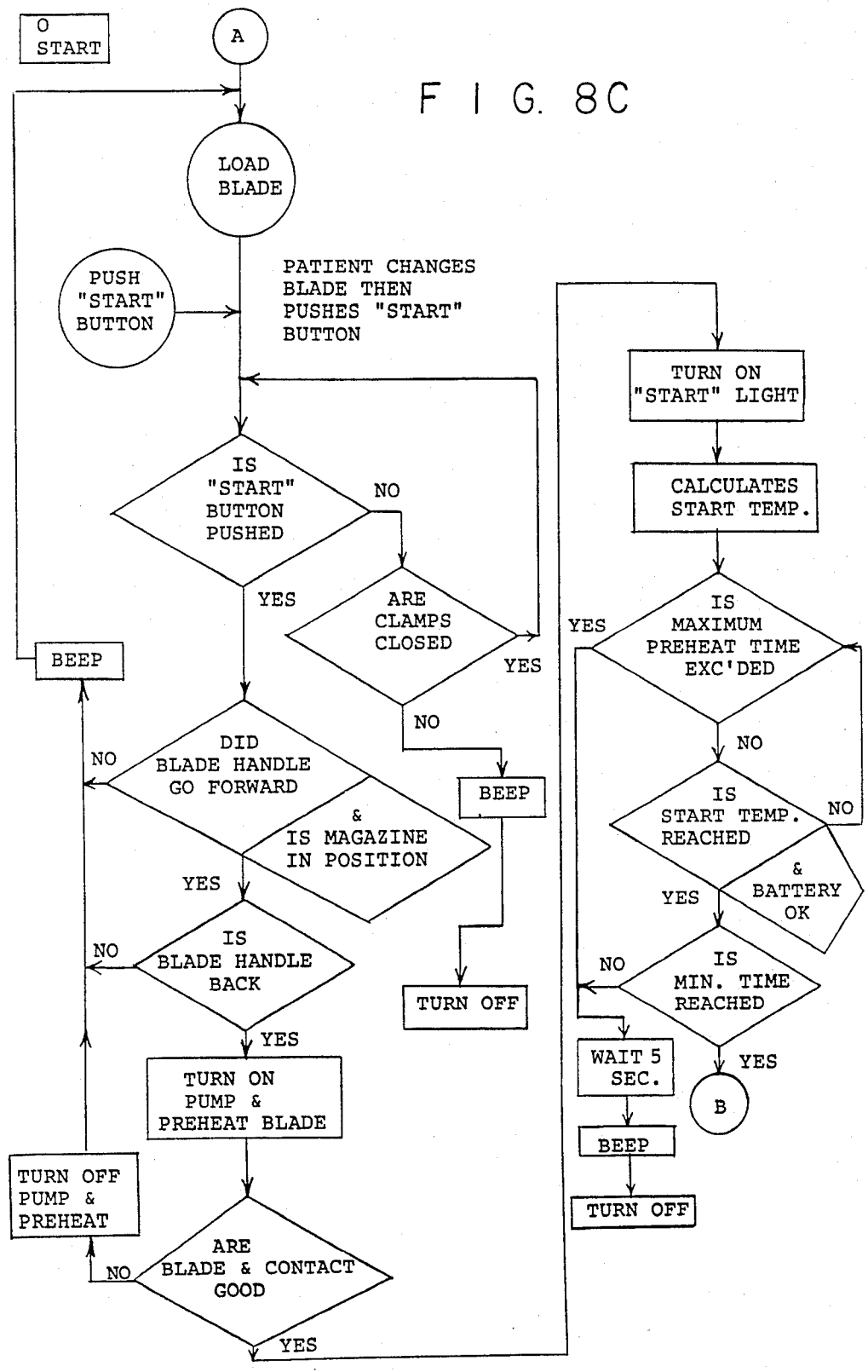
Figure 8D:
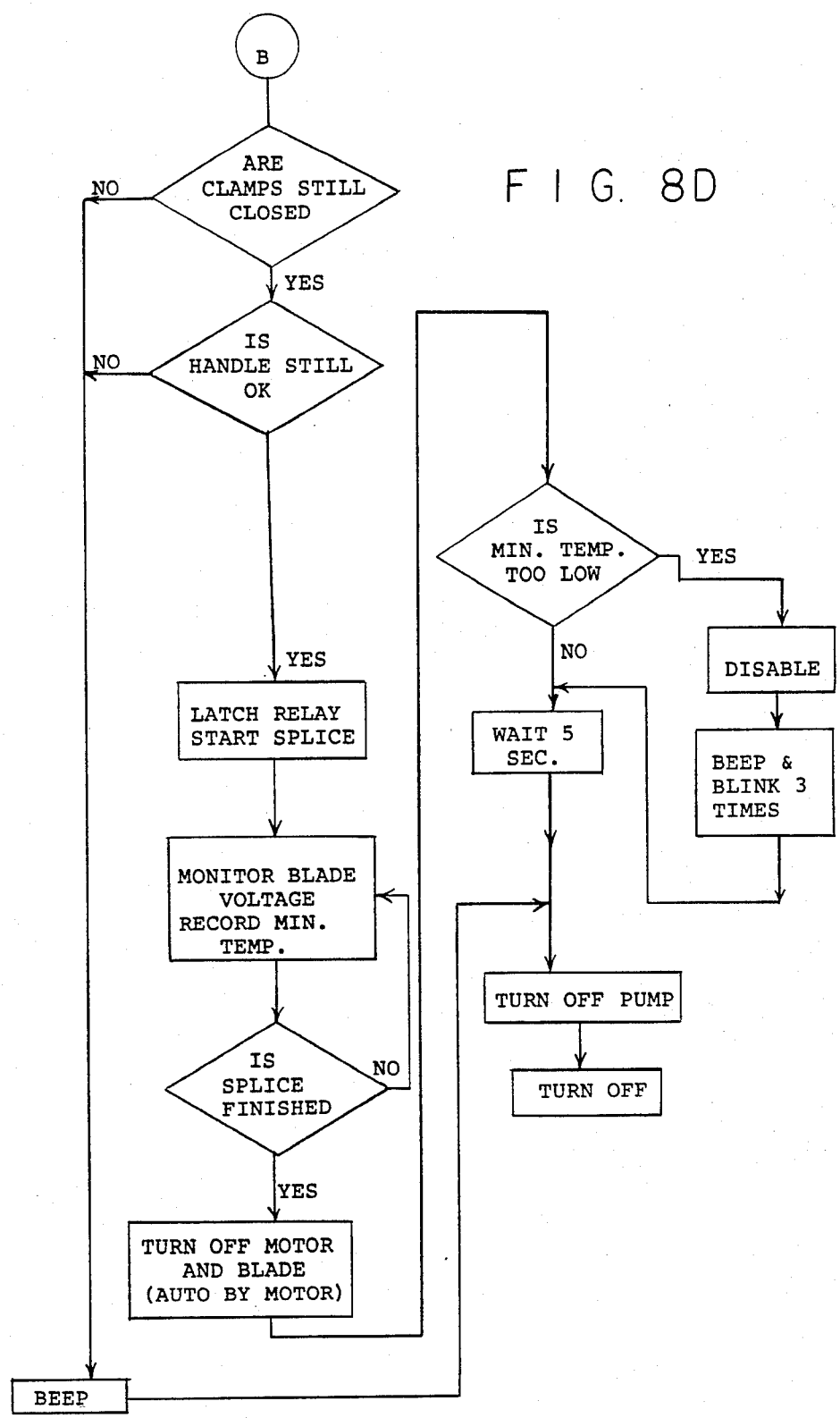

FIG. 7 is a block diagram of the control system of the splicing device described above and includes a controller 26 coupled to a keyboard 66 which includes push buttons 66a, 66b, 66c labelled Battery, Ready and Start, respectively. A battery 64 and its associated charger 64a as well as certain limit switches designated generally as 68 and an analog to digital converter 62 provide inputs to the controller which in turn controls the operation of the heating of knife blade 35 and the operation of cam motor 24 and evacuation pump motor 20. The controller 26 comprises an 8-bit microprocessor No. ID 8085AH, a programmable read only memory No. ID 8755A and a programmable random access memory No. ID 8155H, all by Intel. The A/D converter 62 is a No. ADC 0802LD by National Semiconductor.

With reference to the logic flow diagrams 8A-8D the operation of the automatic splicing device of this invention will be described as it would be used by a CAPD patient.

First of all, it should be noted that to insure patient safety from shock in CAPD applications, the unit is powered by a 24 volt DC rechargeable battery 64 and control circuitry is included that turns off the device in the cycle if the charger 64a is plugged in.

Initially the patient does not have any tubes in the mounting blocks 16, 18 and the unit must be reset from the last splice cycle and the battery condition checked. The patient pushes the "BATTERY" button 66a which causes the control system to check that the battery has an acceptable charge and turn on the motor 24 to rotate a cam cylinder 22 which resets the moveable clamp 16 to the start position and actuates the "home" position switch (not shown). The patient then places the tubes to be spliced in the mounting blocks 16, 18 and latches the covers 40, 42 which actuates switches (not shown) that indicate the mounting blocks are closed.

The patient pushes the "READY" button 66b which causes the control system to turn on the electronics, check that a blade magazine is installed, and check that the mounting block covers are closed.

The patient pushes the blade load/eject level 72 forward which cams open the electrical 39, 39a contacts to the blade 35 and opens the blade clamp 37b, pushes against a blade 35 from the blade magazine 70 which then pushes against other blades in the blade holder to cause the previously used blade 35 to be ejected and a fresh blade to be positioned for the next splice. (NOTE: If the blade magazine is empty, the blade pusher in the magazine mechanically blocks the blade loader/ejector from completing its forward stroke) and actuates a forward switch (not shown) that indicates a fresh blade is properly positioned for the next splice.

The patient retracts the blade load/eject lever 72 which releases the blade clamp 37b to clamp the blade, releases the electrical contacts 39, 39a to press against the blade contact surfaces, releases the next blade in the blade magazine to position it for the next load/eject cycle and actuates a retract switch (not shown) that indicates the lever is retracted and the electrical contacts and blade clamp should be engaged.

The patient pushes the "START" button 66c which causes the control system to turn on the fume evacuation pump 20, check that the blade load/eject lever 72 went forward and back and a magazine 70 was in position, recheck that the tube clamp covers are latched, turn on constant current to the blade and check the voltage after 0.5 seconds to determine if the blade contact and integrity are good. If the above are OK, the control system continues applying constant current to the blade to preheat it for the splice and monitors voltage and time during the preheat cycle to verify the blade integrity and determine when the temperature is right for making a sterile splice. When the proper temperature is reached for the splice, the control system checks that the clamp covers are still closed and the blade load/eject lever is retracted and actuates the splice relay (not shown) that provides a latched electrical circuit for the blade current and motor 24 so the splice can be completed independent of the microprocessor. This latched circuit insures high reliability for the actual splice operation when the sterility of the tubing is being threatened.

The splice motor 24 rotates the cam cylinder 22 which completes a splice and actuates a switch (not shown) that unlatches the splice relay which turns off the motor 24 and blade current.

The control system then turns off the fume evacuation pump motor 20 and checks the minimum voltage monitored during the splicing operation to ensure the temperature remained high enough to guarantee the sterility of the splice and activates an alarm if it isn't.

Figure 9:
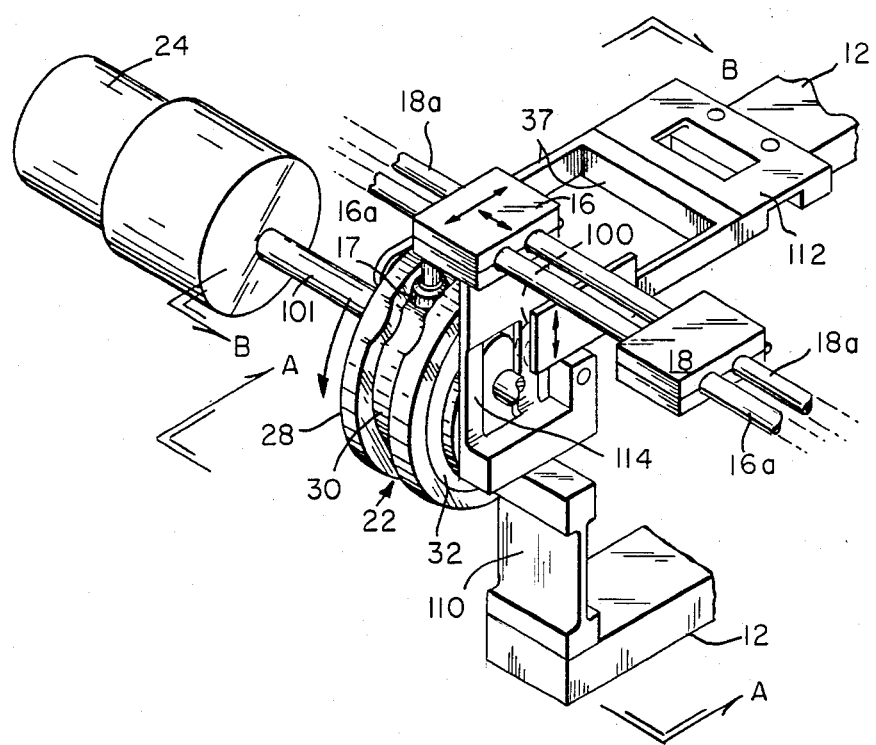
FIG. 9 is an isometric view similar to FIG. 2 showing an alternate embodiment with flexures in place of pivots.

An alternate embodiment is shown in FIGS. 9, 10 and 11. This embodiment employs flexures as substitutes for pivots 102, 105, and 106. More particularly, flexure 110 replaces pivot 102, flexure 112 replaces pivot 105 and flexure 114 replaces pivot 106. The operation with flexures is essentially the same as with the pivots, i.e., providing movement generating three pivotal orthogonal movements.

Figure 12:
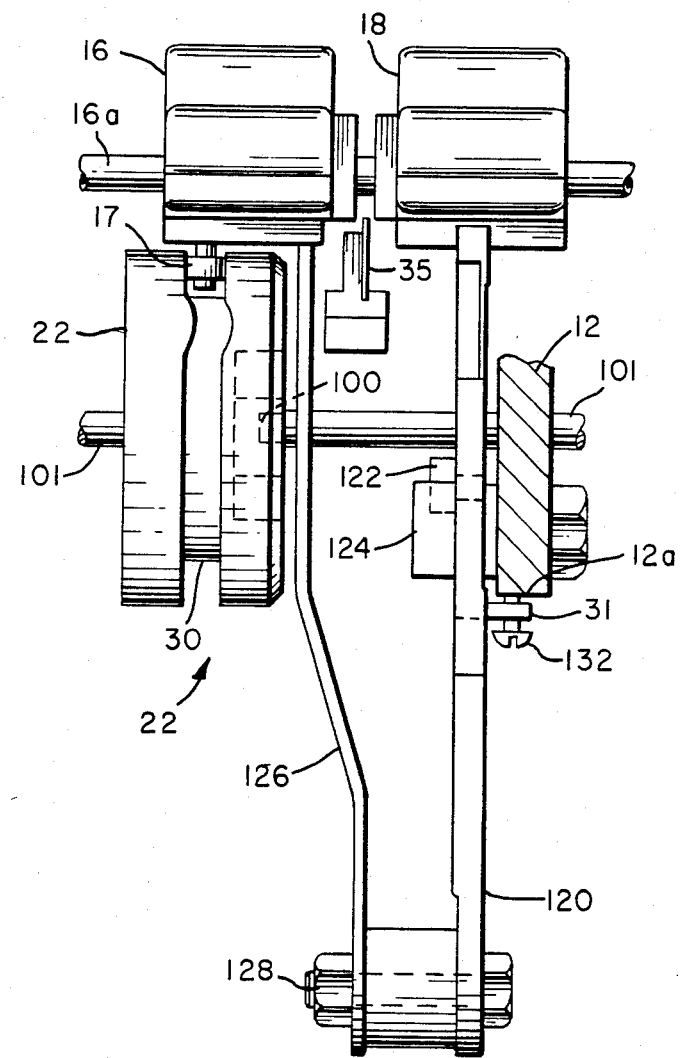

A third embodiment wherein the pivot 106 is replaced with a flexure 126 is shown in FIGS. 12 and 13. More particularly, flexure 126 is flexed by the action of cam follower 17 and is engaged with cam groove 32 by follower 100. Flexure 126 is also attached to movable mounting block 16 as well as being pivotally attached to support 120 at pivot 128. In this manner, the movable and fixed mounting blocks 16, 18 are fastened to each other and only the fixed mounting block 18 is fastened to frame 12. By fastening the mounting blocks 16, 18 to each other, variations in frame mounting holes and in the frame itself are eliminated and as a result assembly and alignment time are less. Standard engineering formulas for calculating stress and deflection were used in designing flexure 126 (Ref. "Engineering Formulas" by K. Gieck, McGraw-Hill, 1971, pp. P3, P4). The support 120 for fixed mounting block 18 is loosely bolted to the frame 12 by means of bolt 122 projecting through slot 123 in support 120 and bolt 124 so that support 120 can pivot around bolt 124. For alignment purposes, i.e., when an aligning force F is applied to pivot 128 (FIG. 13) it causes support 120 to pivot about bolt 124 and pivots flexure 126 around cam follower 100 which is free to translate along the cam groove 32. Since bolt 124 and cam follower 100 are not at the same center, differential movement occurs between support 120 and flexure 126 and when the holders 16 and 18 are in alignment, bolt 122 and pivot 128 are tightened. To provide additional support, screws 130 and 132 threaded through an appendage 131 of support 120 bear on a surface 12a of frame 12. These two screws can be used for fine adjustments about bolt 124.

We claim:

1. A process for forming a connection between two thermoplastic tubes being held in a side-by-side relationship in a pair of displaced mounting blocks movable relative to each other and movable with respect to a heated cutting means between the blocks comprising: passing the cutting means through the tubes; shifting the blocks to align two different cut tube ends facing each other while maintaining contact between the cut tube ends and the cutting means; and withdrawing the cutting means from contact with the tubes while urging the blocks together, said passing, shifting and urging steps being pivotal orthogonal motions; and controlling the timing of said process to automatically obtain said connection.

2. An apparatus for forming a connection between two thermoplastic tubes comprising: a pair of displaced mounting blocks for holding said tubes in a side-by-side relationship; a heated cutting means located between the blocks, said blocks being movable with respect to each other and with respect to the cutting means; means for providing movement between said mounting blocks and said cutting means, said means for providing movement generating three pivotal orthogonal motions; and a controller coupled to the means for providing movement to control the timing of the operation of the apparatus.

3. The apparatus as defined in claim 1, said means for providing movement being a driven cam cylinder containing one groove in each face and one groove around its periphery, one of said mounting blocks being coupled to the groove in one face of said cam and to the groove around the periphery of the cam, said cutting means being coupled to the other face of said cam.

4. The apparatus as defined in claim 1, including an evacuation pump, said mounting blocks having an internal passage in communication at its one end with a separation between said mounting blocks above said tubes, one of said passages being in communication with said pump at its other end the other of said passages being in communication with the atmosphere at its other end.

5. A system for automatically forming a connection between two thermoplastic tubes comprising: a frame; cutting means movably mounted to said frame; means for heating said cutting means; a pair of mounting blocks adapted to receive and hold said tubes in a side-by-side relationship, said blocks being movable relative to each other from a first, to second, and third positions, the cutting means being between the mounting blocks in the first position, said mounting blocks being relatively displaced in said second position to align two different tube ends facing each other, said mounting blocks being separated from said cutting means in said third position while said mounting blocks are urged together; means for providing three pivotal orthogonal motions between the heated cutting means and both of said mounting blocks, said movement passing the cutting means through said tubes when the mounting blocks are in said first position and withdrawing said cutting means from the contact with said tubes when said mounting blocks are in said third position; and a controller coupled to the means for heating the cutting means, and the means for providing movement between the mounting blocks and the cutting means to precisely control the timing of the operation of said system to automatically obtain a connection between the tubes.

6. The system as defined in claim 5, said means for providing movement between the mounting blocks and said cutting means being a driven cylindrical cam containing one groove in each face and one groove around its periphery, one of said mounting blocks being coupled to the groove in one face of said cam and to the groove around the periphery of the cam, said cutting means being coupled to the other face of said cam.

7. The system as defined in claim 5, including an evacuation pump, each of said mounting blocks having an internal passage in communication at its one end with the separation between said mounting blocks above said tubes, one of said passages being in communication with said pump at its other end the other of said passages being in communication with atmosphere at its other end.

8. A system for automatically forming a connection between two thermoplastic tubes comprising: a frame; cutting means movably mounted to said frame; means for heating said cutting means; a pair of mounting blocks adapted to receive and hold said tubes in a side-by-side relationship, said blocks being movable relative to each other; means for moving said mounting blocks from a first, to second, and third positions, the cutting means being between the mounting blocks in the first position, said mounting blocks being relatively displaced in said second position to align two different tube ends facing each other, said mounting blocks being separated from said cutting means in said third position while said mounting blocks are urged together; means for moving the heated cutting means through both of said tubes when the mounting blocks are in said first position and withdrawing said cutting means from the contact with said tubes when said mounting blocks are in said third position; and a controller coupled to the means for heating the cutting means, the means for moving the mounting blocks and the means for moving the cutting means to precisely control the timing of the operation of said system to automatically obtain a connection between the tubes, said means for moving the mounting blocks and said means for moving the cutting means generating three pivotal orthogonal motions.

9. The system as defined in claim 8, said means for moving said mounting blocks and said means for moving said cutting means being a driven cylindrical cam containing one groove in each face and one groove around its periphery, one of said mounting blocks being coupled to the groove in one face of said cam and to the groove around the periphery of the cam, said cutting means being coupled to the other face of said cam.

10. The system as defined in claim 8, including an evacuation pump, each of said mounting blocks having an internal passage in communication at its one end with the separation between said mounting blocks above said tubes, one of said passages being in communication with said pump at its other end the other of said passages being in communication with the atmosphere at its other end.

11. The system as defined in claim 8, the movement of said mounting blocks being a pivoting movement in said second and third positions.

12. A system for automatically forming a sterile connection between two thermoplastic internally sterile tubes comprising: a frame; cutting means pivotally mounted to said frame; means for heating said cutting means; a pair of mounting blocks adapted to receive and hold said tubes one of said blocks being fixed to said frame, the other being movable; means for moving said other mounting block to first, second, and third positions, the cutting means being between the mounting blocks in the first position, said mounting blocks being relatively displaced in said second position to align two different tube ends facing each other, said mounting blocks being separated from said cutting means in said third position while said mounting blocks are urged together; means for moving heated cutting means through both of said tubes when the mounting blocks are in said first position and withdrawing said cutting means from the contact with said tubes when said mounting blocks are in said third position; and a controller coupled to the means for heating the cutting means, the means for moving the mounting blocks and the means for moving the cutting means to precisely control the timing of the operation of said system to automatically obtain a sterile connection between the internally sterile tubes, said means for moving said other mounting block and said means for moving the cutting means generating three pivotal orthogonal motions.

* * * * *